(12) United States Patent
Bouwstra et al.

(10) Patent No.: US 7,596,407 B2
(45) Date of Patent: Sep. 29, 2009

(54) TRANSDERMAL IONTOPHORETIC DELIVERY OF PIPERAZINYL-2(3H)-BENZOXAZOLONE COMPOUNDS

(75) Inventors: Johanna A. Bouwstra, Leiden (NL); Dirk-Jan van den Berg, Leiden (NL); Frederik J. Verbaan, Leiden (NL); Rajkumar V. Conjeevaram, Marietta, GA (US); Ajay K. Banga, Atlanta, GA (US); Viswatej Vemulapalli, Atlanta, GA (US); Hendrik Teunissen, Weesp (NL); Gustaaf J. M. van Scharrenburg, Weesp (NL)

(73) Assignee: Solvay Pharmaceuticals, B.V., Weesp (NL)

( * ) Notice: Subject to any disclaimer, the term of this patent is extended or adjusted under 35 U.S.C. 154(b) by 734 days.

(21) Appl. No.: 11/088,880

(22) Filed: Mar. 25, 2005

(65) Prior Publication Data

US 2005/0234389 A1    Oct. 20, 2005

Related U.S. Application Data

(60) Provisional application No. 60/556,375, filed on Mar. 26, 2004.

(51) Int. Cl.
*A61N 1/30* (2006.01)

(52) U.S. Cl. ..................... 604/20

(58) Field of Classification Search ............ 604/19–22, 604/501, 892.1, 416, 82, 304–308; 607/2, 607/3; 424/447–449
See application file for complete search history.

(56) References Cited

U.S. PATENT DOCUMENTS 5,135,479 A * 8/1992 Sibalis et al. ............ 604/20

(Continued)

FOREIGN PATENT DOCUMENTS

EP    0 522 062 B1    1/1993

(Continued)

OTHER PUBLICATIONS

Feenstra et al., "New 1-Aryl-4-(biarylmethylene) Piperazines as Potential Atypical Antipsychotics Sharing Dopamine $D_2$-Receptor and Serotonin 5-HT $_{1A}$—Receptor Affinities," *Biorganic & Medicinal Chem. Letters* 11:2345-2349 (2001).

(Continued)

*Primary Examiner*—Manuel A Mendez
(74) *Attorney, Agent, or Firm*—Finnegan, Henderson, Farabow, Garrett & Dunner, L.L.P.

(57) ABSTRACT

The invention is related to an iontophoretic method for the delivery of a compound of the formula (I)

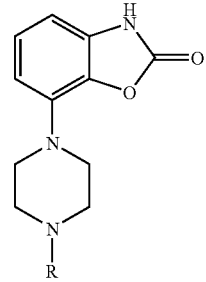

wherein R is defined herein, and pharmaceutically acceptable salts and prodrugs thereof; and, wherein the method comprises: (a) applying a transdermal device to the skin of a living body, wherein the transdermal device has a reservoir containing the compound of formula I or a composition thereof and optionally a pharmaceutically acceptable electrolyte; (b) causing current to flow through the skin so as to iontophoretically deliver the compound of formula I.

The invention is further related to iontophoretic systems and to kits containing the iontophoretic system combined with one or more cartridges containing a compound of formula I, and to cartridges containing a compound of formula I.

29 Claims, 3 Drawing Sheets

7-(4-methyl-1-piperazinyl)-2(3H)-benzoxazolone monohydrochloride flux as a function of its concentration in the absence of NaCl Schematic presentation of the iontophoretic set-up.

U.S. PATENT DOCUMENTS

| | | | |
|---|---|---|---|
| 5,207,752 A | 5/1993 | McNichols et al. | |
| 2004/0013620 A1 | 1/2004 | Charles et al. | |

FOREIGN PATENT DOCUMENTS

| | | |
|---|---|---|
| EP | 0 529 510 A1 | 3/1993 |
| EP | 1 336 406 A | 8/2003 |
| WO | WO 91/15261 | 10/1991 |
| WO | WO 00/29397 A | 5/2000 |
| WO | WO 01/36039 A | 5/2001 |
| WO | WO 01/85168 A | 11/2001 |
| WO | WO 01/85725 A | 11/2001 |
| WO | WO 03/035167 A | 5/2003 |
| WO | WO 2004/045509 A2 | 6/2004 |

OTHER PUBLICATIONS

Johnston et al., "The Novel Dopamine D2 Receptor Partial Agonist, SLV-308, Reverses Motor Disability in MPTP-Lesioned Common Marmosets (*Callithrix Jacchus*)," *British Journal of Pharmacology* 133:133p (2001).

Li, et al., "Iontophoretic Delivery of Apomorphine In Vitro: Physicochemic Considerations," *Pharmaceutical Research* 16(11)1509-1513 (2001).

McCreary et al., "SLV308: A Novel Antiparkinsonian Agent with Antidepressant and Anxiolytic Efficacy," *Society for Neuroscience Abstracts* 27(1):531 (2001).

Olbrich et al., "Antiparkinsonian Antidepressant Anxiolytic Dopamine $D_2$ Partial Agonist 5-HT $_{1A}$Agoist 7-(4-Methyl-1-Piperazinyl) Benzoxazol-2(3H)-one Monohydrochloride: An Evaluation of the Partial Dopamine Agonist Terguride Regarding Positive Symptoms Reduction in Sch," *Drugs of the Future* 26(2):128-132 (2001).

Tyle, P., "Iontophoretic Devices for Drug Delivery," *Pharmaceutical Research*, 3(6):318-326 (1986).

Wolf, "SLV-308, Solvay," *Current Opinion in Investigational Drugs*, 4(7):878-882 (2003).

\* cited by examiner

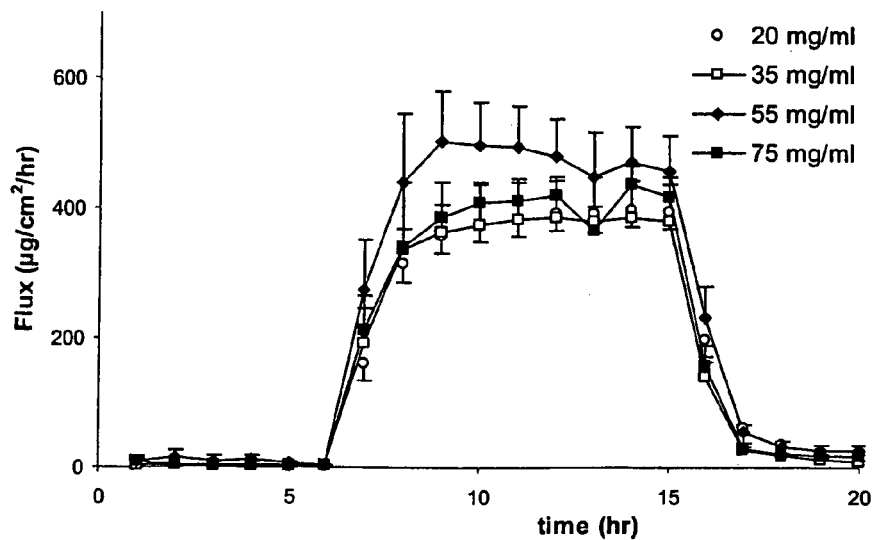
Figure 1. 7-(4-methyl-1-piperazinyl)-2(3H)-benzoxazolone monohydrochloride flux as a function of its concentration in the absence of NaCl
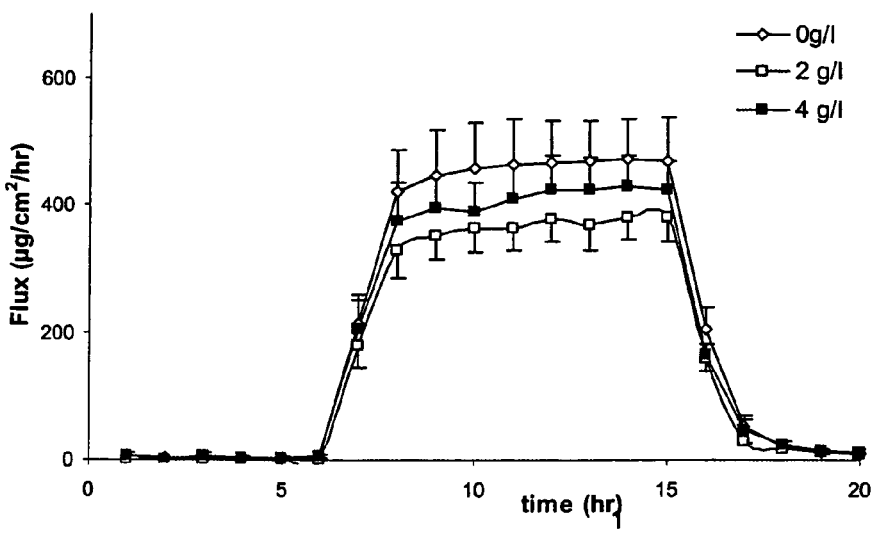
Figure 2. 7-(4-methyl-1-piperazinyl)-2(3H)-benzoxazolone monohydrochloride flux at a concentration of 35 mg/ml in the presence of 0, 2 and 4 g/l NaCl

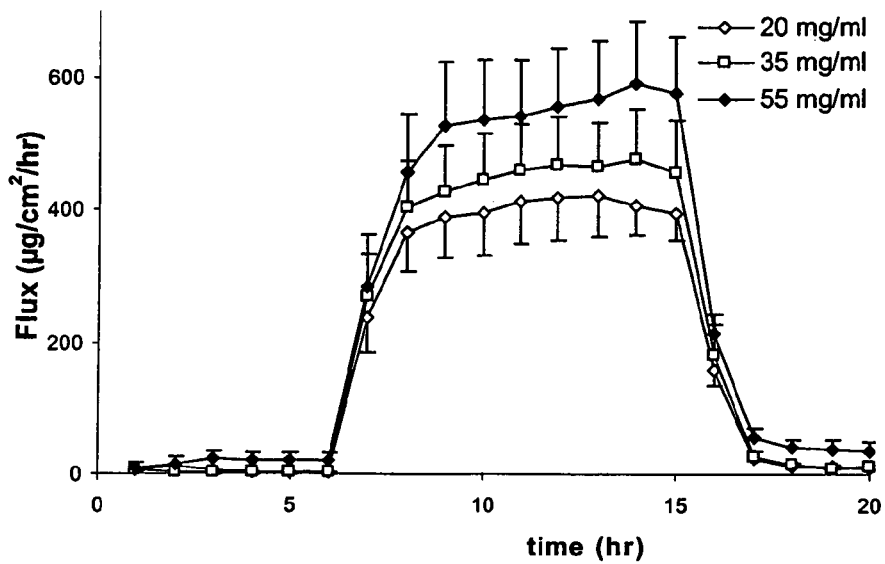
Figure 3. 7-(4-methyl-1-piperazinyl)-2(3H)-benzoxazolone monohydrochloride flux as a function of its concentration in the presence of 4 g/l NaCl
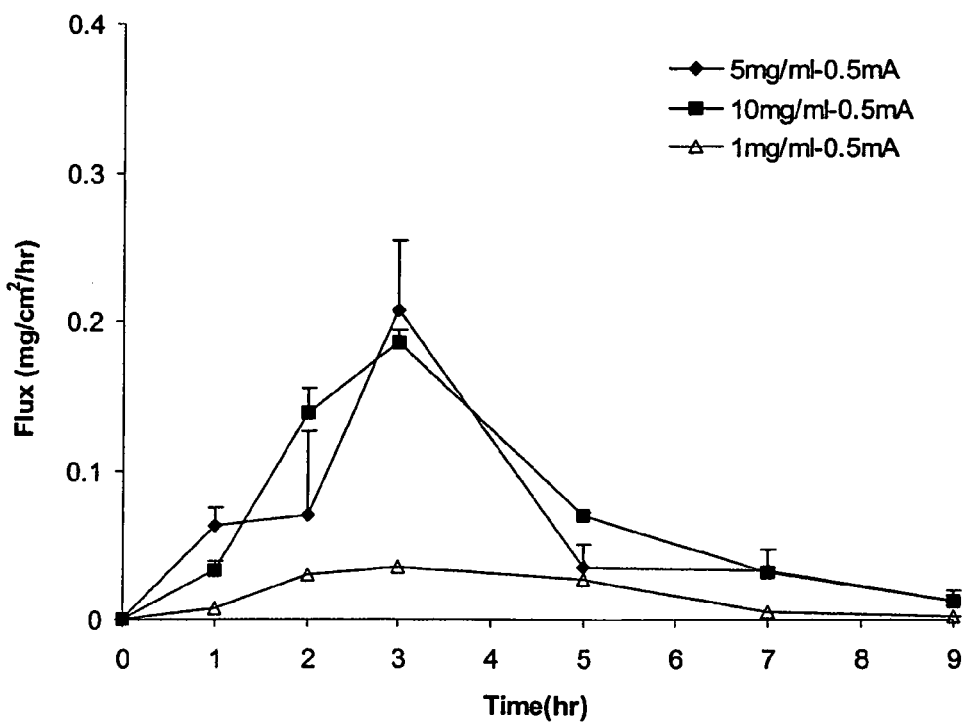
Figure 4. 7-(4-benzyl-1-piperazinyl)-2(3H)- benzoxazolone mesylate flux as a function of its concentration in the presence of 30 mM NaCl.

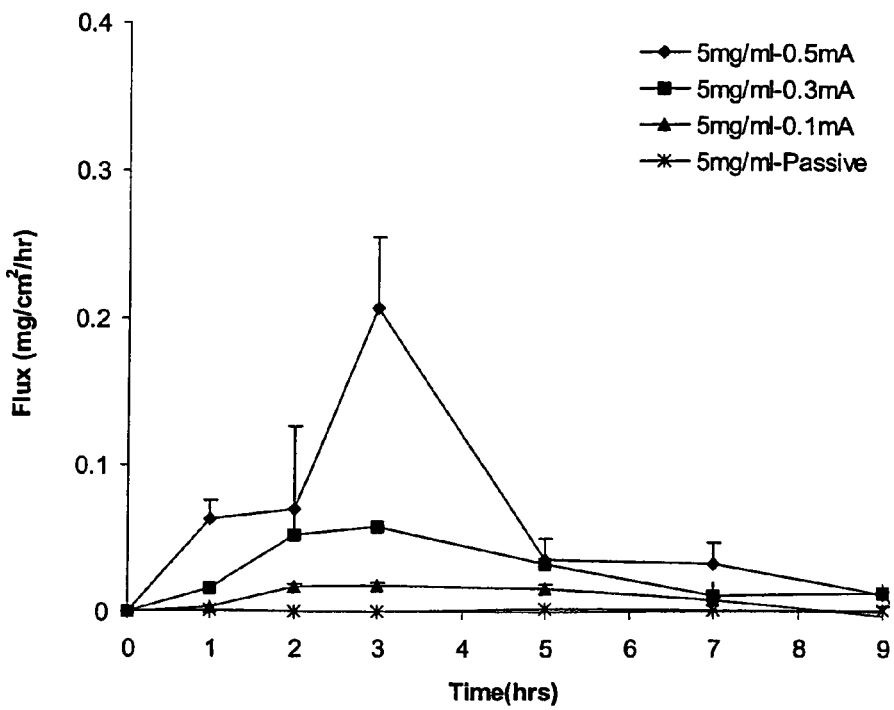
Figure 5. 7-(4-benzyl-1-piperazinyl)-2(3H)- benzoxazolone mesylate flux as a function of the current density in the presence of 30 mM NaCl.
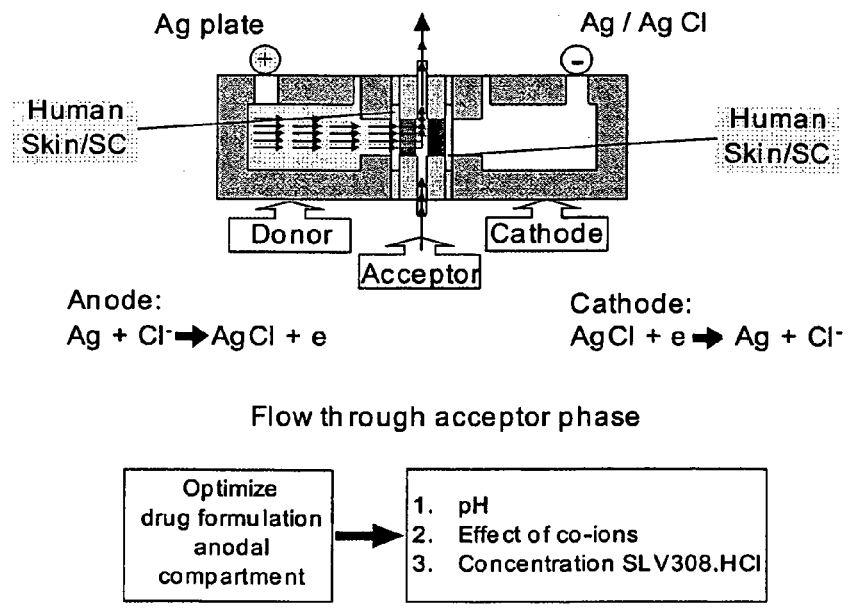
Figure 6. Schematic presentation of the iontophoretic set-up.

TRANSDERMAL IONTOPHORETIC DELIVERY OF PIPERAZINYL-2(3H)-BENZOXAZOLONE COMPOUNDS

This application claims benefit of priority of U.S. Provisional Application No. 60/556,375, filed on Mar. 26, 2004, the disclosure of which is incorporated by reference herein.

FIELD OF THE INVENTION

The present invention relates to transdermal iontophoretic delivery of pharmaceutical compounds of the general formula

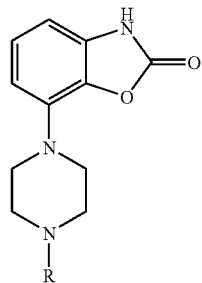

(I)

wherein
R is
methyl, ethyl, ethyl substituted with one or more fluorine atoms, or cyclo-($C_{3-7}$)-alkylmethyl optionally substituted with one or more fluorine atoms, or a benzyl, 2-pyridylmethyl, 3-pyridylmethyl or 4-pyridylmethyl radical optionally substituted with one or more substituents which are the same or different and are independently chosen from
halogen, hydroxyl, cyano, amino, mono-$C_{1-3}$-alkylamino, di-$C_{1-3}$-alkylamino, $C_{1-3}$-alkoxy, $CF_3$, $OCF_3$, $SCF_3$, $C_{1-4}$-alkyl, $C_{1-3}$-alkylsulfonyl amino, phenyl, furanyl and thienyl, and wherein said substituents phenyl, furanyl and thienyl are optionally substituted with 1-3 moieties which are the same alike or different and are independently chosen from
hydroxy, halogen, $C_{1-4}$-alkoxy, $C_{1-4}$-alkyl, cyano, aminocarbonyl, mono-$C_{1-4}$-alkylaminocarbonyl, and di-$C_{1-4}$-alkylaminocarbonyl;

and pharmaceutically acceptable salts and prodrugs thereof.

The invention also relates to transdermal iontophoretic delivery of pharmaceutical compounds of the general formula (I) wherein
R is
methyl, ethyl, ethyl substituted with one or more fluorine atoms, or cyclo-($C_{3-7}$)-alkylmethyl optionally substituted with one or more fluorine atoms or a benzyl, 2-pyridylmethyl, 3-pyridylmethyl or 4-pyridylmethyl radical, which radicals are optionally substituted with one or more substituents that are the same or different and are independently chosen from
halogen, hydroxyl, cyano, amino, mono-$C_{1-3}$-alkylamino, di-$C_{1-3}$-alkylamino, $C_{1-3}$-alkoxy, $CF_3$, $OCF_3$, $SCF_3$, $C_{1-4}$-alkyl, and $C_{1-3}$-alkylsulfonyl amino.

The present invention also relates to a method for controlling the delivery profile of pharmaceutical compounds of the general formula (I) and compositions thereof, and the use of said controlled delivery profiles in the treatment of pain disorders, for example restless leg syndrome and CNS disorders, such as Parkinson's disease. R can be chosen from methyl and benzyl, in which benzyl is optionally substituted with 1-3 substituents which are the same or different and are independently chosen from hydroxyl and halogen. The present invention also relates to compounds wherein R is unsubstituted methyl or benzyl.

BACKGROUND OF THE INVENTION

Compounds of the general formula I as defined above are known from WO00/29397 and WO01/85725. These compounds show varying activities as either partial agonists or agonists at the dopamine $D_2$ receptor and are also agonists of the $5HT1_A$ receptor. These combinations of activities make the compounds of value for the treatment of afflictions and diseases of the central nervous system caused by disturbances in either the dopaminergic or serotonergic systems, for example, in Parkinson's disease and restless leg syndrome.

In certain cases, e.g., when oral delivery or injection of a particular pharmaceutically active compound (also referred to as a drug) may be ineffective or unacceptable because of poor gastrointestinal absorption, an extensive first pass effect, patient pain and discomfort, or other side effects or drawbacks, transdermal delivery may provide an advantageous method of delivering that compound. This is the case, for example, for Parkinson's disease, where there is a need to administer medication to patients who are sleeping, comatose or anaesthetized. Further, there is growing evidence that continuous dopamine stimulation avoids the development of problems associated with intermittent dosing and where continuous drug delivery has been shown to decrease the incidence of "off" periods (P. Niall and W. H. Oertel, Congress Report of 7th International Congress of Parkinson's Disease and Movement Disorders, Miami, Fla., Nov. 10-14, 2002). In general, transdermal administration also has its problems, since it is not always easy to get drugs to cross the skin.

Iontophoretic transdermal delivery relates to introducing ions or soluble salts of pharmaceutically active compounds into tissues of the body under the influence of an applied electric field.

The features and benefits of iontophoretic transdermal delivery systems as compared with passive transdermal systems, as well as with other means of delivering pharmaceutical compounds into the bloodstream have e.g. been reviewed in O. Wong, "Iontophoresis: Fundamentals," in Drugs Pharm. Sci. (1994), 62 (Drug Permeation Enhancement), 219-46 (1994); P. Singh et al., "Iontophoresis in Drug Delivery: Basic Principles and Applications", Critical Reviews in Therapeutic Drug Carrier Systems, 11 (2 & 3): 161-213 (1994); and Ajay K. Banga, Electrically Assisted Transdermal and Topical Drug Delivery, Taylor and Francis Group Ltd., London UK, 1998, ISBN 0-7484-0687-5.

In certain cases, e.g., when transdermal delivery by means of patches appears to be ineffective or unacceptable because of low passage through the skin, leading to very large patches, iontophoretic transdermal delivery may provide an advantageous method of delivering that compound. Further iontophoretic transdermal delivery has the major advantage that the administered amount can be regulated precisely and can be used to easily titrate patients up to a certain level of administration over a period of up to several weeks.

Despite these advantages, iontophoretic methods appear limited as the drug delivery profile of a particular method depends heavily on the particular drug administered. Although a lot of experiments have been done with the iontophoretic delivery of various active substances, specific information allowing a person skilled in the art to tailor the delivery profile of a specific drug is not always available.

As it has appeared that it is very difficult to develop transdermal patches with an acceptable size for compounstipkds with the general formula (I), there is a need for an iontophoretic delivery method for said compounds that allows variable rate delivery of said compounds tailored to a specific treatment.

SUMMARY OF THE INVENTION

The present invention relates to iontophoretic transdermal technology that provides for the delivery of the compounds of the general formula (I) and compositions thereof through human skin.

One embodiment of the present invention may provide, for example, a method for the delivery of a compound of the general formula (I) and pharmaceutically acceptable salts and prodrugs thereof, wherein the method includes applying a transdermal device to the skin of a living body, wherein the transdermal device has a reservoir comprising at least one compound of the general formula (I) and compositions thereof and optionally a pharmaceutically acceptable electrolyte; and causing current to flow through the skin so as to iontophoretically deliver at least one compound of the general formula (I) and compositions thereof.

Another embodiment of the invention may provide an iontophoretic system for the delivery of at least one compound of the general formula (I) and compositions thereof through the skin, wherein the system comprises a transdermal delivery device attachable to the skin, the device comprising a first electrode and a second electrode, and a reservoir for containing a pharmaceutically acceptable electrolyte and at least one of the compounds of the general formula (I) and compositions thereof in electrical communication with the first and second electrodes; and a means for connecting to an electrical power source to the first and second electrodes; wherein the reservoir may contain at least one of the compounds of the general formula (I) and compositions thereof and optionally a pharmaceutically acceptable electrolyte.

Another embodiment of the invention may provide a kit comprising the iontophoretic system combined with one or more cartridges comprising at least one compound of the general formula (I) or a kit containing one or more cartridges comprising at least one compound of the general formula (I) to be used for refilling the reservoir of the iontophoretic system. The number of cartridges in a kit is not limited. The number of cartridges in the kits can be at least 2, at least 7, or at least 14, for example. In some embodiments, the number of cartridges may be no more than 91, or no more than 28, for example.

The skin through which the delivery has to take place is animal skin, for example human skin.

BRIEF DESCRIPTION OF THE FIGURES

FIG. 1 plots the flux of 7-(4-methyl-1-piperazinyl)-2(3H)-benzoxazolone across human stratum corneum as a function of the active compound concentration versus time.

FIG. 2 plots the flux of 7-(4-methyl-1-piperazinyl)-2(3H)-benzoxazolone across human stratum corneum as a function of the electrolyte concentration versus time.

FIG. 3 plots the flux of 7-(4-methyl-1-piperazinyl)-2(3H)-benzoxazolone across human stratum corneum as a function of active compound concentration versus time in the presence of 4 g/l NaCl.

FIG. 4 plots the flux of 7-(4-benzyl-1-piperazinyl)-2(3H)-benzoxazolone mesylate across hairless rat skin as a function of active compound concentration versus time in the presence of 30 millimolar (mM) NaCl.

FIG. 5 plots the flux of 7-(4-benzyl-1-piperazinyl)-2(3H)-benzoxazolone mesylate across hairless rat skin as a function of the current density in the presence of 30 mM NaCl.

FIG. 6 depicts a schematic presentation of the iontophoretic set-up used for the tests with 7-(4-methyl-1-piperazinyl)-2(3H)-benzoxazolone.

DETAILED DESCRIPTION OF INVENTION

An iontophoretic transdermal delivery system may comprise a first (donor) electrode containing an electrolytically available active compound within a suitable vehicle or carrier and optionally a penetration enhancer, a counter electrode and a power source, the first and second electrodes each being in electrically conductive communication with the power source. The first and second electrodes can be adapted for spaced apart physical contact with the skin whereby, in response to a current provided by the power source through the electrodes, a therapeutic amount of the active compound is administered through the skin to a patient.

It has surprisingly been found that the iontophoretic delivery (dose and profile) by which a particular active compound of the general formula (I) is administered to a patient may be controlled by suitable combination of the initial concentration of the drug and electrolyte and the applied current (constant/variable) in the iontophoretic system. For example, it has been found that the combination of current density (constant/variable) and the initial amount of electrolyte may lead to an iontophoretic device with a very reasonable size that allows the drug delivery profile to be adjusted. The ability to tailor the drug delivery profile in iontophoresis may provide increased control of the drug's effects on the user. Additionally, the ability to tailor drug delivery profile in iontophoresis may make the iontophoretic delivery of the compounds of formula (I) a more practically effective mode of administration.

As used herein, the term "permeation profile" means a plot of the flux of the active compound versus time for a given delivery period.

As used herein, the term "cartridge" means a container containing the active compound that is used for storage of the active compound before it is delivered by the device. In at least one embodiment of the present invention, a cartridge can be selected for its user-friendliness. Any means for packaging the active compound separately from the iontophoretic device may be considered a "cartridge." For example, detachable and replaceable reservoirs may be used to deliver active compound to the device.

The electrolytes used in the methods of the present invention may include univalent or divalent ions, for example. Examples of electrolytes used in our method include all Cl⁻ donating compounds that are water soluble, such as HCl, NaCl, KCl, $CaCl_2$, $MgCl_2$, triethylammonium chloride and tributylammonium chloride. In some embodiments, the electrolyte comprises NaCl. The required amount of electrolyte may depend on factors such as the transport area of the device, the volume of the vehicle or carrier, the concentration of the active compound, the current density, the duration of the iontophoresis and the efficiency of the transport. The electrolyte may be present in amounts of, for example, at least about 0.005 mmole, at least about 0.01 mmole, or at least about 0.05 mmole. The electrolyte may be present in amounts of, for example, not more than about 2 mmole, not more than about 1.0 mmole, or not more than about 0.3 mmole. The initial amount of electrolyte may be expressed as a concentration of, for example, at least about 0.005 M, at least about 0.01 M, or at least about 0.03 M. The initial amount of electrolyte may be expressed as a concentration of, for example, not more than about 2 M, not more than about 0.2 M, or not more than about 0.2 M.

The compounds that may be administered in accordance with the present invention were already defined above. Prodrugs of the compounds mentioned above are within the scope of the present invention. Prodrugs are therapeutic agents which are inactive per se but are transformed into one or more active metabolites. Prodrugs are bioreversible derivatives of drug molecules used to overcome some barriers to the utility of the parent drug molecule. These barriers include, but are not limited to, solubility, permeability, stability, presystemic metabolism and targeting limitations (Medicinal Chemistry: Principles and Practice, 1994, ISBN 0-85186494-5, Ed.: F. D. King, p. 215; J. Stella, "*Prodrugs as therapeutics*", Expert Opin. Ther. Patents, 14(3), 277-280, 2004; P. Ettmayer et al., "*Lessons learned from marketed and investigational prodrugs*", J. Med. Chem., 47, 2393-2404, 2004). Pro-drugs, i.e., compounds which when administered to humans by any known route, are metabolized to compounds having formula (I), belong to the invention. In particular this relates to compounds with primary or secondary amino or hydroxy groups. Such compounds can be reacted with organic acids to yield compounds having formula (I) wherein an additional group is present which is easily removed after administration, for instance, but not limited to amidine, enamine, a Mannich base, a hydroxylmethylene derivative, an O-(acyloxymethylene carbamate) derivative, carbamate, ester, amide or enaminone.

As stated above, the compounds of formula I can be used in the form of pharmaceutically acceptable salts derived from inorganic or organic acids. Salts of prodrugs also fall within the scope of this invention. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. Pharmaceutical Sciences, 1977, 66: 1 et seq. The salts can be prepared in situ during the final isolation and purification of the compounds of the invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, mesylate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Active drugs that may be administered by the method described herein include, but are not limited to, compounds such as 7-(4-methyl-1-piperazinyl)-2(3H)-benzoxazolone or its monohydrochloride salt (SLV308, see Drugs of the Future 2001, 26, 128-32) and 7-(4-benzyl-1-piperazinyl)-2(3H)-benzoxazolone or its monomesylate salt (SLV318).

7-(4-methyl-1-piperazinyl)-2(3H)-benzoxazolone or its monohydrochloride salt and 7-(4-benzyl-1-piperazinyl)-2(3H)-benzoxazolone or its monomesylate salt are suitable for the treatment of restless leg syndrome or Parkinson's disease.

Compounds of the formula (I), prodrugs, pharmaceutically acceptable salts of either of the foregoing, and mixtures of two or more of the foregoing can be administered in accordance with the invention.

The pH of the solution in the drug reservoir may be at least about 3.0 in some embodiments. In other embodiments, the pH may be less than or equal to about 7.5.

In still other embodiments, the pH may range from about 4.0 to about 6.5. The pH can be maintained on a constant level by means of a buffer such as a citrate buffer or a phosphate buffer.

For 7-(4-methyl-1-piperazinyl)-2(3H)-benzoxazolone or its monohydrochloride salt, a useful pH ranges from about 5.0 to about 6.0. Another possible pH for said compound is about 5.5. For 7-(4-benzyl-1-piperazinyl)-2(3H)— benzoxazolone or its monomesylate salt, the pH may range, for example, from about 3.5 to about 6.0. Another useful pH for said compound is about 4.0.

During the delivery period, the current may be caused to flow by applying a constant, pulsed, or alternating voltage/current. Alternatively, the current may be caused to increase during the delivery period in order to titrate an increasing concentration of the compound of formula (I).

The voltage charged in the current application step is selected in the range of voltage that does not injure the skin of a living body and that does not disadvantage the rate of the transdermal absorption of the active compound. The voltage can be, for example, at least about 0.1 V, or at least about 0.5 V, or at least about 1 V. The voltage also can be, for example, less than about 40 V, or less than about 20 V, or less than about 10 V.

The pulsed or alternating voltage may have a frequency of, for example, at least about 0.01 Hz, or at least about 100 Hz, or at least about 5 kHz. The pulsed or alternating voltage may have a frequency of, for example, no more than about 200 kHz, or no more than about 100 kHz, or no more than about 80 kHz. The pulsed or alternating voltage may use substantially any type of waveform shape, including for example, sine, square, triangular, sawtooth, rectangular, etc. In addition, the pulsed or alternating voltage may be applied on a duty cycle less than 100%.

The current density can be, for example, at least about 0.001 mA/cm$^2$, or at least about 0.005 mA/cm$^2$, or at least about 0.025 mA/cm$^2$. The current density also can be, for example, not more than about 1.0 mA/cm$^2$, not more than about 0.8 mA/cm$^2$ or not more than about 0.5 mA/cm$^2$.

The drug reservoir contains the drug and optional electrolyte with, as the vehicle or carrier, either an aqueous solution or a (hydro)gel. The reservoir gel may be comprised of water soluble polymers or hydrogels. In principle any gel can be used. Gels can be selected so that they do not adversely affect the skin (corrosion and irritation). Gels may exhibit suitable properties, such as good skin contact (adhesiveness) and electroconductive property. Non-limiting examples include agar, agarose, polyvinyl alcohol, or crosslinked hydrogels, such as Hydroxypropylmethylcellulose (HPMC), Methylcellulose (MC), Hydroxyethylcellulose (HEC), Carboxymethylcellulose (CMC) and Polyvinylpyrrolidone (PVP) and Polyvinyl Acetate Phthalate (PVAP).

Suitable skin penetration enhancers include those well known in the art, and for example, include $C_2$-$C_4$ alcohols such as ethanol and isopropanol; surfactants, e.g., anionic surfactants such as salts of fatty acids of 5 to 30 carbon atoms, e.g. sodium lauryl sulphate and other sulphate salts of fatty acids, cationic surfactants such as alkylamines of 8 to 22 carbon atoms, e.g. oleylamine, and nonionic surfactants such as polysorbates and polyoxamers; aliphatic monohydric alcohols of 8 to 22 carbon atoms such as decanol, lauryl alcohol, myristyl alcohol, palmityl alcohol, linolenyl alcohol and oleyl alcohol; fatty acids of 5 to 30 carbon atoms such as oleic acid, stearic acid, linoleic acid, palmitic acid, myristic acid, lauric acid and capric acid and their esters such as ethyl caprylate, isopropyl myristate, methyl laurate, hexamethylene palmitate, glyceryl monolaurate, polypropylene glycol monolaurate and polyethylene glycol monolaurate; salicylic acid and its derivatives; alkyl methyl sulfoxides such as decyl methyl sulfoxide and dimethyl sulfoxide; 1-substituted azacycloalkan-2-ones such as 1-dodecylazacyclo-heptan-2-one (AZONE®); amides such as octylamide, oleicamide, hexamethylene lauramide, lauric diethanolamide, polyethylene glycol 3-lauramide, N,N-diethyl-m-toluamide and crotamiton; and any other compounds compatible with compounds of the general formula (I) and the devices and having transdermal permeation enhancing activity.

In an alternative embodiment the carrier or vehicle is separated from the skin by a membrane. This membrane may be chosen, for example, to have a low resistance against the electric current, and/or to avoid substantially raising the barrier against the transport of the active compound, and/or to contain the carrier within the device during storage and transport. A low resistance against the electronic current may be defined in one embodiment as 20% of the resistance of the skin. The barrier against transport of the active compound is not substantially raised by the membrane when the flux of active compound in the membrane containing device is, for example, more than 75% compared with the device not containing a membrane. Examples of membranes that can be used are e.g., the membranes having low electrical resistance as disclosed in D. F. Stamiatialis et al., J. Controlled Release 2002, 81, 335-345, such a the membranes CT-10 kDA, CT-20 kDA, PES-30 kDA and PSf-100 kDA of Sartorius, Dialysis-5 kDA of Diachema, CA-10 kDa, CA-25 kba, CA-50 kD and CA-100 kDa of Amika and NF-PES-10 and NF-CA-30 of Nadir Filtration.

The iontophoretic systems used to practice the subject invention may include devices and/or components selected from a wide variety of commercially available devices or components and/or from a wide range of methods and materials such as taught, for example, by patents and publications relating to such iontophoretic systems. In particular, the iontophoretic transdermal system may comprise an iontophoretic device such as is available from The Alza corporation of Mountain View, Calif., U.S.A. (E-trans® Transdermal Technology), Birch Point Medical Inc. of St. Paul, Minn. U.S.A. (e.g., IontoPatch™ working according to the Wearable Electronic Disposable Delivery (WEDD™) technology), Iomed of Salt Lake City, Utah, U.S.A. (e.g. IOMED™ Phoresor devices using IOGEL®), TransQ®Flex, TransQ®E, TransQ®1&2 or Numby Stuff® electrodes and the GelSponge®) containment medium), or a device such as manufactured by Vyteris of Fair Lawn, N.J., U.S.A. (Active Transdermal system) or a device such as manufactured by Empi of St. Paul, Minn. (e.g. Empi DUPEL™), or a device known as the LECTRO™ Patch, manufactured by General Medical Device Corp. of Los Angeles, Calif.

The electrodes may comprise reactive or non-reactive electrodes. Examples of reactive electrodes are those made from metal salts, such as silver chloride or materials described in U.S. Pat. No. 4,752,285. The silver chloride electrodes can be prepared based on the knowledge of a person skilled in the art or are available from Iomed. Alternative reactive electrodes can be made from a combination of ion-exchange resins, exemplified by electrodes available from Empi. Examples of non-reactive electrodes are those made from metals such as gold or platinum, or from carbon particles dispersed in polymeric matrices such as one used in the LECTRO™ Patch. Adhesives used to fix the iontophoretic device to the skin may comprise pressure sensitive adhesives used in passive transdermal delivery systems, such those derived from silicone or acrylic polymers, or those derived from rubbers such as polyisobutylene. A combination of pressure sensitive and conductive adhesives can also be used, such as those described EPA 0542294.

In the drug reservoir, the concentration of the drug may be, for example, at least about 0.1 mg/ml. The concentration of the drug in the drug reservoir may be, for example, not more than about 90 mg/ml. In some embodiments, the concentration for 7-(4-methyl-1-piperazinyl)-2(3H)-benzoxazolone or its monohydrochloride salt is, for example, about 10 to about 75 mg/ml. In other embodiments, that concentration ranges from about 20 to about 55 mg/ml. In still other embodiments, the concentration for 7-(4-benzyl-1-piperazinyl)-2(3H)-benzoxazolone or its monomesylate is, for example, about 1 to about 30 mg/ml. In other embodiments, that concentration can range from about 5 to about 10 mg/ml.

Additionally, the drug reservoir of the iontophoretic system may include further additives. Such additives can be chosen from those that are well known and conventional in the iontophoresis art. Such additives include, for example, antimicrobial agents, preservatives, antioxidants, penetration enhancers and buffers.

An example of a unit dosage that may be delivered during a single delivery period may vary in amount. For example, a unit dosage in one embodiment may be at least about 0.05 mg. The unit dosage in another embodiment may be, for example, no more than about 100 mg. A unit dosage for 7-(4-methyl-1-piperazinyl)-2(3H)-benzoxazolone or its monohydrochloride in some embodiments can range from about 0.05 to about 60 mg. In other embodiments, that concentration can range from about 0.05 to about 30 mg.

The unit dosage that is delivered may be determined on the basis of one or more of a wide range of factors, including, for example, the compound, condition, age, body weight, clearance, etc.

The flux rate of delivery through the skin of at least one compound of formula I can be, for example, at least about 50 μg per hour. In other embodiments, the flux rate of delivery through the skin can be, for example, no more than about 4000 μg per hour.

In some embodiments of the present invention, the iontophoretic delivery method of pharmaceutical compounds comprises a drug delivery treatment protocol that includes periodically applying an iontophoretic transdermal device at intervals that may be as frequent as twice daily or as infrequent as once a week or once a month. In what is herein referred to as a single treatment step, the device is applied, the drug is iontophoretically delivered and the device is then removed. Although the absolute quantity of the drug delivered may vary substantially, a unit dosage is herein defined to be that quantity of drug, however large or small, that is delivered during a single treatment step by a single device application at an individual site.

During a single treatment step, the drug may be delivered constantly or during defined intervals. The intervals may range, for example, from about 10 minutes to 24 hours. In some cases it may be advantageous to omit delivery during a part of the day and night cycle, e.g., during the night for 6, 7 or 8 hours.

Upon starting the administration of a drug, it may be desirable to have a linear or stepwise increase of the drug over a certain time starting with a low amount of drug up to the normal maintenance dose, which time is also referred to as titration time. The period for titration can be, for example, at least 3 days or not more than 42 days. The period for titration can range between 7 and 21 days in some embodiments, and in still other embodiments around 14 days. The iontophoretic delivery method according to the present invention may be useful for such a linear or stepwise increase of the drug administration as the administered amount of drug can be regulated by linear or stepwise increase of the current density.

In some embodiments, the iontophoretic system comprises
(a) a transdermal delivery device attachable to the skin, the device comprising a first electrode and a second electrode, and a reservoir capable of comprising a compound of the formula I as set forth above, and optionally a pharmaceutically acceptable electrolyte, in electrical communication with the first and second electrodes, and
(b) means for connecting an electrical power source to the first and second electrodes.

The electrical power source may be any appropriate source, such as for example, a battery, a rechargeable battery, or electrical power delivered by an electrical outlet. The means for connecting the electrical power source may comprise any suitable conductor, conduit, or carrier of electrical energy. The means may comprise, for example, wiring, a power adaptor, a power controller, a power monitor, or a combination of two or more of the foregoing.

The iontophoretic system may comprise still other methods and materials, such as described in WO 92/17239, EPA 0547482 and U.S. Pat. No. 4,764,164, the entire contents of which are incorporated herein by reference.

In some embodiments, the transport area of the device can be at least about 1.0 cm$^2$.

In other embodiments, the transport area might be no more than about 30 cm$^2$. In still other embodiments, the transport area can range from about 2 to about 15 cm$^2$, and in still other embodiments from about 5 to about 10 cm$^2$.

In another embodiment of the invention, the drug reservoir of the iontophoretic system is delivered empty to the user and the reservoir is filled just before or after application of the system to the skin. When using this embodiment the iontophoretic system is combined in a kit with a number of cartridges containing the compound of general formula I as defined above, including a salt or prodrug thereof, or a composition of two or more thereof and optionally a pharmaceutically acceptable electrolyte. This kit, which may also be defined as a starter kit, may contain one or more cartridges comprising at least one active compound. The number of cartridges in one kit can range, for example, from 7 to 91, and in other embodiments from 14 to 28. The compound and the optional electrolyte may be in the form of a solid crystalline, amorphous or lyophilized material which material has to be dissolved in water before filling of the reservoir of the iontophoretic device, or in the form of a solution ready for use. The iontophoretic system may be refilled with a fresh solution for example every 3-48 hours, or for example once every 24 hours. In another embodiment, for example, a kit which is intended for more than one treatment step, as long as the iontophoretic system is working properly, only one or more of cartridges comprising the compound of general formula I as defined above, including a salt or prodrug thereof, or a composition thereof and optionally a pharmaceutically acceptable electrolyte may be present.

As used herein, the term "about" when modifying a value indicates the variability inherent in that value that would be understood by one of ordinary skill in the art. For example, "about" indicates that significant digits, rounding errors, and the like provide a range of values about the recited number that falls within the scope of the disclosure of that number.

The following examples are only intended to further illustrate the invention, in more detail, and therefore these examples are not deemed to restrict the scope of the invention in any way.

EXAMPLES

Example 1

General Methods

Human Stratum Corneum Isolation

Human Stratum Corneum (HSC) was prepared from dermatomed healthy human skin. Within 24 hours after surgical removal of the human skin (abdominal or breast), residual subcutaneous fat was removed. To avoid interference with contaminating subcutaneous fat, the skin surface was carefully wiped with a tissue paper soaked in 70% ethanol. The skin was dermatomed to a thickness of about 300 μm using a Padgett Electro Dermatome Model B (Kansas City, USA). It was then incubated with the dermal side on Whatman paper soaked in a solution of 0.1% trypsin in PBS overnight at 4° C. and subsequently for 1 hour at 37° C. Then HSC was peeled off from the underlying epidermis and dermis. Remaining trypsin activity was blocked by bathing HSC in a 0.1% trypsin inhibitor solution in PBS, pH 7.4. HSC was washed several times in water and stored in a silica gel containing desiccator in a $N_2$ environment to inhibit oxidation of lipids.

Hairless Rat Skin Isolation

Hairless rats were euthanized by inhalation of carbon dioxide using an exposure chamber designed for such use half hour before start of experiment. The skin from the abdomen was carefully removed, making sure no muscle or fat was attached to the skin. The skin was then cut into small squares to fit the Franz diffusion set (Membrane Transport System, PermeGear, U.S.A) and placed in 0.1 M potassium phosphate buffer until mounted.

Active Compound Synthesis 7-(4-methyl-1-piperazinyl)-2(3H)-benzoxazolone hydrochloric acid salt was synthesized as described in WO00/29397 and Drugs of the Future 2001, 26, 128-32. 7-(4-benzyl-1-piperazinyl)-2(3H)-benzoxazolone mesylate was prepared as described in WO01/85725 and WO02/066449. The disclosure of the four foregoing documents are incorporated by reference herein.

Solutions in Iontophoresis Experiments 7-(4-methyl-1-piperazinyl)-2(3H)-benzoxazolone as a HCl salt was dissolved in 10 mM sodium citrate solution. The pH was adjusted to pH 5.5 with 10 mM citric acid. 7-(4-benzyl-1-piperazinyl)-2(3H)-benzoxazolone as a mesylate salt was dissolved in 0.1 M potassium phosphate buffer. The pH was adjusted to pH 4.0 using o-phosphoric acid.

Iontophoresis Experiments with
7-(4-methyl-1-piperazinyl)-2(3H)-benzoxazolone

Iontophoresis experiments with 7-(4-methyl-1-piperazinyl)-2(3H)-benzoxazolone were performed using 9-channel computer controlled power supply to provide constant current (Electronics Department, Gorlaeus Laboratories, Leiden University, The Netherlands.) Alternatively the commercial available Power Supply PCT-MK1 of Moor Instruments, UK can be used. A silver plate electrode was used as an anode (e.g. Silver foil >99.99% pure, 1.0 mm thick (Aldrich article nr. 36,943-8), 5 cm long, 3 mm wide) and a silver/silver chloride electrode (prepared by repeatedly (2 or 3 times) dipping silver wire (>99.99% pure, Ø 1.0 mm (Aldrich art. Nr. 26,559-4), bended at the tip to produce a small projection (approx. 3 mm) at a right angle to the vertical electrode shaft in melted silver chloride powder (>99.999% pure, Aldrich art. Nr. 20,438-2) as a cathode. (Alternatively, the silver plate and silver/silver chloride electrodes can be prepared according to chapter 3.4.3. of Ajay K. Banga, Electrically Assisted Transdermal and Topical Drug Delivery, Taylor and Francis Group Ltd., London UK, 1998, ISBN 0-7484-0687-5. or can be purchased from a commercial supplier such as Iomed.)

All diffusion experiments were carried out at a constant current density of 0.5 mA/cm$^2$, using three chambers continuous flow through diffusion cells at room temperature. The diffusion set up consisted of a peristaltic pump, a fraction collector and 8 diffusion cells (for diffusion cell see FIG. 4). Stratum corneum was used for all diffusion studies. Human stratum corneum was hydrated for two hours in PBS pH 7.4 prior to mounting in the cells. Two pieces of stratum corneum were placed between the anodal and acceptor side, and between acceptor and cathodal side, with the apical side facing the anodal and cathodal compartments. Dialysis membrane (cut off 5,000 D) was used as supporting membrane for the stratum corneum. Parafilm rings were added for making a tight connection between the compartments. The temperature of the acceptor chamber was 37° C. The flow of PBS through the acceptor chamber was kept approximately constant for each cell during the experiment: 6-8 ml per hour. After six hours of passive diffusion, the current was switched on. The current was switched off at t=15 h. During a period of another 5 hours (post iontophoretic period) passive diffusion post iontophoresis was carried out. During iontophoresis, the current density was 0.5 mA/cm$^2$. The total resistance of the stratum corneum sheets was monitored during the experiment with two additional silver electrodes. A very low resistance is indicative of leakage of the stratum corneum in a cell. When this was observed, the diffusion data obtained were discarded. All conditions were repeated at least 3 times. The number of skin donors used for each condition was at least 3.

Iontophoresis Experiments with
7-(4-benzyl-1-piperazinyl)-2(3H)-benzoxazolone

Iontophoresis experiments with 7-(4-benzyl-1-piperazinyl)-2(3H)-benzoxazolone were performed using vertical Franz diffusion cells (Membrane Transport System, PermeGear, U.S.A) hooked up to a Keithley 2400 source meter and the current monitored using a multimeter. The donor half of the cell was exposed to room temperature (25° C.) while the receptor half was maintained at 37° C. Receptor compartment was continuously stirred. Freshly excised hairless rat skin was mounted on the vertical diffusion cells, after the receptor compartment had been filled with a suitable receptor media, which can maintain the sink condition. The receptor media had the same composition as the donor solution without the drug, so that the sink conditions could be maintained. The formulation was placed in the donor compartment. A silver wire was used as the anode in the donor and a silver/silver chloride wire was used as the cathode in the receptor. Current was applied for 3 hours using a constant current power source. However, sampling was continued till 24 hrs to see if enhanced delivery will stop on terminating current. Samples were taken at pre-determined time intervals from the receptor and analyzed by the HPLC as described below. Samples were replaced with fresh receptor medium and this was taken into consideration in the calculations.

HPLC Analysis 7-(4-methyl-1-piperazinyl)-2(3H)-benzoxazolone was analyzed using HPLC with UV detection (Waters Chromatography, Etten Leur, The Netherlands). A Chromsep SS column was used (250*3 mm L*i.d.) thermostatted at 30° C. The mobile phase consisted of acetonitrile/methanol/0.7 g/l ammonium acetate buffer at pH 5.6 (Dec. 6, 1982 v/v) and was used at 0.5 ml/min. The detection wavelength was 215 nm. No oxidation or degradation products of the compound were observed in the chromatograms of the sample solutions.

7-(4-benzyl-1-piperazinyl)-2(3H)-benzoxazolone was analyzed using HPLC with UV detection (Waters Alliance system). A Chromsep SS column was used (150*3 mm L*i.d.) with particle size of 5 μm thermostatted at 40° C. The mobile phase was made using 1.54 g ammonium acetate in 460 ml of water (pH adjusted to 4.6 using acetic acid) and 540 ml of methanol and degassed. The flow rate was 0.5 ml/min. The detection wavelength was 243 nm. Injection volume was 10 μl.

Example 2

Iontophoresis of
7-(4-methyl-1-piperazinyl)-2(3H)-benzoxazolone
monohydrochloride with Varying Active Substance
Concentration A solution of 75 mg/ml of 7-(4-methyl-1-piperazinyl)-2 (3H)-benzoxazolone monohydrochloride in citrate buffer was prepared (This is 85% of the maximum solubility of 7-(4-methyl-1-piperazinyl)-2(3H)-benzoxazolone monohydrochloride in citrate buffer at pH 5.5). From this solution further dilutions were made in citrate buffer pH 5.5. The concentrations tested were: 20 mg/ml, 35 mg/ml, 55 mg/ml and 75 mg/ml.

As can be observed in FIG. 1, after switching on the current, there is a steep increase in 7-(4-methyl-1-piperazinyl)-2(3H)-benzoxazolone flux. During the iontophoresis period, the 7-(4-methyl-1-piperazinyl)-2(3H)-benzoxazolone fluxes observed were extremely high. The mean transport during the iontophoretic period was 394±26, 383±42, 459±59, 418±31 μg/hr/cm$^2$ for the donor concentrations of 20, 35, 55, 75 mg/ml respectively. There was no significant difference between these values as tested by one way ANOVA (p-value between all groups >0.05).

The pH of the donor solution did not change more than 0.2 pH units during the experiment.

Example 3

Iontophoresis of 7-(4-methyl-1-piperazinyl)-2(3H)-benzoxazolone monohydrochloride with Varying Active Electrolyte Concentration 7-(4-methyl-1-piperazinyl)-2(3H)-benzoxazolone monohydrochloride was dissolved in 10 mM sodium citrate solution. The pH was adjusted to pH 5.5 with 10 mM citric acid. Sodium chloride was added resulting in solutions of either 0, 2 or 4 mg/ml NaCl. The 7-(4-methyl-1-piperazinyl)-2(3H)-benzoxazolone monohydrochloride concentration was kept constant, namely 35 mg/ml. At 4 mg/ml NaCl, the selected 7-(4-methyl-1-piperazinyl)-2(3H)-benzoxazolone monohydrochloride concentration is 80% of its maximum solubility. The solubility of 7-(4-methyl-1-piperazinyl)-2(3H)-benzoxazolone monohydrochloride increases with reducing NaCl concentration.

FIG. 2 illustrates that, after switching on the current, there is a steep increase in 7-(4-methyl-1-piperazinyl)-2(3H)-benzoxazolone flux. During the iontophoresis period, the 7-(4-methyl-1-piperazinyl)-2(3H)-benzoxazolone fluxes observed were extremely high. The mean transport during the iontophoretic period was 471±65, 377±37 and 424±50 µg/hr/cm$^2$ (averages±s.e.m.) for the sodium chloride concentrations 0, 2, 4 mg/ml, respectively. There was no significant difference between these values as tested by one way ANOVA (p-value between all groups >0.05). The pH of the donor solution did not change more than 0.2 pH units during the experiment.

The strong increase and decrease during switching on and off the current indicates that a large variation in transport can be achieved by iontophoresis.

Example 4

Iontophoresis of 7-(4-methyl-1-piperazinyl)-2(3H)-benzoxazolone monohydrochloride with Varying Active Substance Concentration in the Presence of 4 g/l NaCl A solution of 55 mg/ml of 7-(4-methyl-1-piperazinyl)-2(3H)-benzoxazolone monohydrochloride in citrate buffer was prepared (This is 85% of the maximum solubility of 7-(4-methyl-1-piperazinyl)-2(3H)-benzoxazolone monohydrochloride in citrate buffer at pH 5.5 in the presence of 4 g/l NaCl). From this solution further dilutions were made in citrate buffer pH 5.5. The concentrations tested were: 20 mg/ml, 35 mg/ml, 55 mg/ml and NaCl was added in amount to yield a concentration of 4 g/l.

FIG. 3 shows that in the presence of NaCl the iontophoretic flux of 7-(4-methyl-1-piperazinyl)-2(3H)-benzoxazolone monohydrochloride was slightly dependent on its concentration flux. The fluxes were 409±47, 467±74 and 580±87 µg/hr/cm$^2$ for the donor concentrations of 20, 35 and 55 mg/ml respectively (averages±s.e.m.). However, the trend appeared to be not statistically significant as tested by one way ANOVA (p-value between all groups >0.05).

The pH of the donor solution did not change more than 0.2 pH units during the experiment.

Example 5

Iontophoresis of 7-(4-benzyl-1-piperazinyl)-2(3H)-benzoxazolone Varying Active Substance Concentration in the Presence of 30 mM NaCl A solution of 10 g/ml of 7-(4-benzyl-1-piperazinyl)-2(3H)-benzoxazolone mesylate in phosphate buffer was prepared (This is about the maximum solubility of 7-(4-methyl-1-piperazinyl)-2(3H)-1benzoxazolone monohydrochloride in phosphate buffer at pH 4.0 in the presence of 30 mM NaCl). From this solution further dilutions were made in phosphate buffer pH 4.0. The concentrations tested were: 1 mg/ml, 5 mg/ml, and 10 mg/ml and NaCl was added in amount to yield a concentration of 30 mM.

FIG. 4 shows that there is an increase in iontophoretic flux with an increase from 1 mg/ml to 5 mg/ml in active substance concentration and that there is no increase in iontophoretic flux on further increase in active substance concentration to 10 mg/ml.

Example 6

Iontophoresis of 7-(4-benzyl-1-piperazinyl)-2(3H)-benzoxazolone at a Concentration of 5 mg/ml, Varying Current Density in the Presence of 30 mM NaCl The solution of 5 g/ml of 7-(4-benzyl-1-piperazinyl)-2(3H)-benzoxazolone mesylate in phosphate buffer as prepared in example 5 was used to study the effect of the current density. Fluxes where measured at current densities of 0, 0.1, 0.3 and 0.5 mA. FIG. 5 shows that iontophoresis considerably enhances the permeation of 7-(4-benzyl-1-piperazinyl)-2(3H)-benzoxazolone as compared to passive delivery. Further it is shown that there is a linear relationship between flux and current density.

The invention claimed is:

1. An iontophoretic method for the delivery of at least one compound of the formula

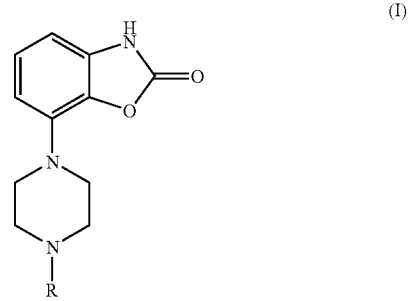

(I)

wherein R is methyl, ethyl, ethyl substituted with one or more fluorine atoms, or cyclo-($C_{3-7}$)-alkylmethyl optionally substituted with one or more fluorine atoms, or a benzyl, 2-pyridylmethyl, 3-pyridylmethyl or 4-pyridylmethyl radical optionally substituted with one or more substituents which are the same or different and are independently chosen from halogen, hydroxyl, cyano, amino, mono-$C_{1-3}$-alkylamino, di-$C_{1-3}$-alkylamino, $C_{1-3}$-alkoxy, $CF_3$, $OCF_3$, $SCF_3$, $C_{1-4}$-alkyl, $C_{1-3}$-alkylsulfonyl amino, phenyl, furanyl and thienyl and wherein said substituents phenyl, furanyl and thienyl are optionally substituted with 1-3 moieties which are the same or different and are chosen from hydroxy, halogen, $C_{1-4}$-alkoxy, $C_{1-4}$-alkyl, cyano, aminocarbonyl, mono-$C_{1-4}$-alkylaminocarbonyl and di-$C_{1-4}$-alkylaminocarbonyl;

at least one prodrug thereof, at least one pharmaceutically acceptable salt of either of the foregoing, or a mixture of any of the foregoing, wherein the method comprises:

(a) applying a transdermal device to the skin of a living body, wherein the transdermal device comprises a reservoir comprising the at least one compound of formula I as set forth above and optionally a pharmaceutically acceptable electrolyte;

(b) causing current to flow through the skin so as to iontophoretically deliver to the living body the at least one compound of formula I as set forth above.

2. The method according to claim 1, wherein R is methyl, ethyl, ethyl substituted with one or more fluorine atoms, or cyclo-$(C_{3-7})$-alkylmethyl optionally substituted with one or more fluorine atoms, or a benzyl, 2-pyridylmethyl, 3-pyridylmethyl or 4-pyridylmethyl radical, which radicals are optionally substituted with one or more substituents that are alike or different and are independently chosen from halogen, hydroxyl, cyano, amino, mono-$C_{1-3}$-alkylamino, di-$C_{1-3}$-alkylamino, $C_{1-3}$-alkoxy, $CF_3$, $OCF_3$, $SCF_3$, $C_{1-4}$-alkyl, and $C_{1-3}$-alkylsulfonyl amino.

3. The method according to claim 1, wherein a constant current is caused to flow.

4. The method according to claim 1, wherein a variable current is caused to flow.

5. The method according to claim 4, wherein an increasing current is caused to flow.

6. The method according to claim 1, wherein the at least one compound of formula I is delivered to the living body at a flux rate ranging from about 50 µg per hour to about 4000 µg per hour.

7. The method according to claim 1, wherein the at least one compound of formula I comprises 7-(4-methyl-1-piperazinyl)-2(3H)-benzoxazolone, a pharmaceutically acceptable salt thereof, or a mixture of the foregoing.

8. The method according to claim 7, wherein the at least one compound of formula I comprises (7-(4-methyl-1-piperazinyl)-2(3H)-benzoxazolone) monohydrochloride.

9. The method according to claim 1, wherein the at least one compound of formula I comprises 7-(4-benzyl-1-piperazinyl)-2(3H)-benzoxazolone, a pharmaceutically acceptable salt thereof, or a mixture of the foregoing.

10. The method according to claim 9, wherein the at least one compound of formula I comprises (7-(4-benzyl-1-piperazinyl)-2(3H)-benzoxazolone) monomethanesulphonate.

11. The method according to claim 1, wherein the current flows through the skin at a current density ranging from about 0.001 mA/cm² to about 1.0 mA/cm².

12. The method according to claim 1, wherein the reservoir comprises the at least one compound of formula I in a composition at an initial concentration ranging from about 0.1 mg/ml to about 90 mg/ml.

13. The method according to claim 1, wherein the reservoir comprises the at least one compound of formula I in a composition, and the pH of the composition ranges from about 3.5 to about 7.5.

14. The method according to claim 1, wherein an amount ranging from about 0.1 mg to about 100 mg of the compound of formula I is delivered through the skin during step (b).

15. The method according to claim 1 wherein the current is caused to flow for a time period ranging from about 10 minutes to about 24 hours.

16. The method according to claim 7, wherein the method is applied to a human for the treatment or prophylaxis of Parkinson's disease or restless leg syndrome.

17. The method according to claim 16, wherein the compound of formula I comprises 7-(4-methyl-1-piperazinyl)-2(3H)-benzoxazolone monohydrochloride.

18. The method according to claim 9, wherein the method is applied to a human for the treatment or prophylaxis of Parkinson's disease or restless leg syndrome.

19. The method according to claim 18, wherein the compound of formula I comprises 7-(4-benzyl-1-piperazinyl)-2(3H)-benzoxazolone monohydrogenmesylate.

20. An iontophoretic system for the delivery of at least one compound of formula I through skin, the compound of formula I having the structure:

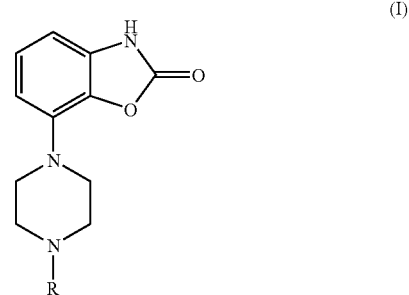

(I)

wherein R is methyl, ethyl, ethyl substituted with one or more fluorine atoms, or cyclo-$(C_{30.7})$-alkylmethyl optionally substituted with one or more fluorine atoms, or a benzyl, 2-pyridylmethyl, 3-pyridylmethyl or 4-pyridylmethyl radical optionally substituted with one or more substituents which are alike or different and are independently chosen from halogen, hydroxyl, cyano, amino, mono-$C_{1-3}$-alkylamino, di-$C_{1-3}$-alkylamino, $C_{1-3}$-alkoxy, $CF_3$, $OCF_3$, $SCF_3$, $C_{1-4}$-alkyl, $C_{1-3}$-alkylsulfonyl amino, phenyl, furanyl and thienyl and wherein said substituents phenyl, furanyl and thienyl are optionally substituted with 1-3 moieties which are alike or different and are chosen from hydroxy, halogen, $C_{1-4}$-alkoxy, $C_{1-4}$-alkyl, cyano, aminocarbonyl, mono-$C_{1-4}$-alkylaminocarbonyl and di-$C_{1-4}$-alkylaminocarbonyl;

at least one prodrug thereof, at least one pharmaceutically acceptable salt of either of the foregoing, or a mixture of any of the foregoing, wherein the iontophoretic system comprises:

(a) a transdermal delivery device attachable to the skin, the device comprising a first electrode and a second electrode, and a reservoir capable of comprising a compound of the formula I as set forth above, and optionally a pharmaceutically acceptable electrolyte, in electrical communication with the first and second electrodes, and (b) means for connecting an electrical power source to the first and second electrodes.

21. The iontophoretic system of claim 20, further comprising a membrane capable of closing the reservoir.

22. The iontophoretic system of claim 20, wherein the compound of formula I comprises 7-(4-methyl-1-piperazinyl)-2(3H)-benzoxazolone or a pharmaceutically acceptable salt thereof.

23. The iontophoretic system of claim 20, wherein the compound of formula I comprises 7-(4-benzyl-1-piperazinyl)-2(3H)-benzoxazolone or a pharmaceutically acceptable salt thereof.

24. The iontophoretic system of claim 20, wherein the reservoir comprises the compound of formula I and optionally a pharmaceutically acceptable electrolyte in a composition having a pH ranging from about 3.5 to about 7.5.

25. The iontophoretic system of claim 20, wherein the compound of formula I is present in the reservoir in a composition at a concentration ranging from about 0.1 to about 90 mg/ml.

26. A kit comprising
(1) an iontophoretic system for the delivery of a compound through skin, comprising
    (a) a transdermal delivery device attachable to the skin, the device including a first electrode and a second electrode, and a reservoir able to contain a composition of an active compound, and
    (b) a electrical power source connected to the first and second electrodes, and
(2) one or more cartridges comprising a compound of formula I

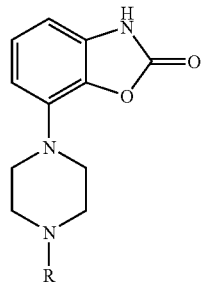

wherein R is
methyl, ethyl, ethyl substituted with one or more fluorine atoms, or cyclo-($C_{3-7}$)-alkylmethyl optionally substituted with one or more fluorine atoms, or a benzyl, 2-pyridylmethyl, 3-pyridylmethyl or 4-pyridylmethyl radical optionally substituted with one or more substituents which are alike or different and are independently chosen from halogen, hydroxyl, cyano, amino, mono-$C_{1-3}$-alkylamino, di-$C_{1-3}$-alkylamino, $C_{1-3}$-alkoxy, $CF_3$, $OCF_3$, $SCF_3$, $C_{1-4}$-alkyl, $C_{1-3}$-alkylsulfonyl amino, phenyl, furanyl and thienyl and wherein said substituents phenyl, furanyl and thienyl are optionally substituted with 1-3 moieties which are alike or different and are chosen from hydroxy, halogen, $C_{1-4}$-alkoxy, $C_{1-4}$-alkyl, cyano, aminocarbonyl, mono-$C_{1-4}$-alkylaminocarbonyl and di-$C_{1-4}$-alkylaminocarbonyl;

at least one prodrug thereof, at least one pharmaceutically acceptable salt of either of the foregoing, or a mixture of any of the foregoing, and optionally a pharmaceutically acceptable electrolyte.

27. A cartridge capable of filling or refilling an iontophoretic system for the delivery of a compound through skin, the cartridge comprising at least one compound of formula I

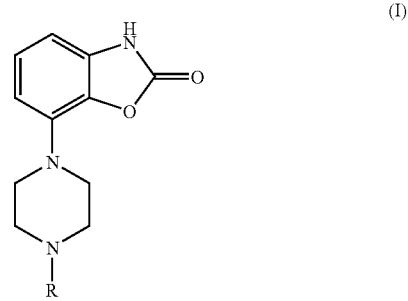

wherein R is
methyl, ethyl, ethyl substituted with one or more fluorine atoms, or cyclo-($C_{3-7}$)-alkylmethyl optionally substituted with one or more fluorine atoms, or a benzyl, 2-pyridylmethyl, 3-pyridylmethyl or 4-pyridylmethyl radical optionally substituted with one or more substituents which are alike or different and are independently chosen from halogen, hydroxyl, cyano, amino, mono-$C_{1-3}$-alkylamino, di-$C_{1-3}$-alkylamino, $C_{1-3}$-alkoxy, $CF_3$, $OCF_3$, $SCF_3$, $C_{1-4}$-alkyl, $C_{1-3}$-alkylsulfonyl amino, phenyl, furanyl and thienyl and wherein said substituents phenyl, furanyl and thienyl are optionally substituted with 1-3 moieties which are alike or different and are chosen from hydroxy, halogen, $C_{1-4}$-alkoxy, $C_{1-4}$-alkyl, cyano, aminocarbonyl, mono-$C_{1-4}$-alkylaminocarbonyl and di-$C_{1-4}$-alkylaminocarbonyl;

at least one prodrug thereof, at least one pharmaceutically acceptable salt of either of the foregoing, or a mixture of any of the foregoing, and optionally a pharmaceutically acceptable electrolyte.

28. The cartridge according to claim 27, wherein the at least one compound of formula I comprises 7-(4-methyl-1-piperazinyl)-2(3H)-benzoxazolone or a pharmaceutically acceptable salt thereof.

29. The cartridge according to claim 27, wherein the at least one compound of formula I is present in the cartridge in a composition at a concentration ranging from about 0.1 to about 90 mg/ml.

* * * * *

UNITED STATES PATENT AND TRADEMARK OFFICE
CERTIFICATE OF CORRECTION

| | |
|---|---|
| PATENT NO. | : 7,596,407 B2 |
| APPLICATION NO. | : 11/088880 |
| DATED | : September 29, 2009 |
| INVENTOR(S) | : Bouwstra et al. |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 734 days.

Delete the phrase "by 734 days" and insert -- by 1223 days --

Signed and Sealed this

Fifteenth Day of June, 2010

David J. Kappos
*Director of the United States Patent and Trademark Office*